(12) United States Patent
Stylos et al.

(10) Patent No.: US 7,996,084 B2
(45) Date of Patent: Aug. 9, 2011

(54) IMPLANTABLE MEDICAL DEVICE WITH AUTOMATIC ISCHEMIA THRESHOLD DETERMINATION

(75) Inventors: Lee Stylos, Stillwater, MN (US); Todd J. Sheldon, North Oaks, MN (US); Steven N. Lu, Fridley, MN (US); William J. Combs, Minnetonka, MN (US); Robert J. Nehls, Lakeville, MN (US)

(73) Assignee: Medtronic, Inc., Minneapolis, MN (US)

( * ) Notice: Subject to any disclaimer, the term of this patent is extended or adjusted under 35 U.S.C. 154(b) by 1314 days.

(21) Appl. No.: 11/379,290

(22) Filed: Apr. 19, 2006

(65) Prior Publication Data

US 2007/0250127 A1    Oct. 25, 2007

(51) Int. Cl.
*A61N 1/08* (2006.01)
(52) U.S. Cl. .............................. 607/9; 607/19
(58) Field of Classification Search ............. 607/9, 19
See application file for complete search history.

(56) References Cited

U.S. PATENT DOCUMENTS

| | | | |
|---|---|---|---|
| 5,016,632 A * | 5/1991 | Hoegnelid et al. | 607/19 |
| 6,129,746 A | 10/2000 | Levine et al. | |
| 6,256,538 B1 | 7/2001 | Ekwall | |
| 6,264,606 B1 | 7/2001 | Ekwall et al. | |
| 6,604,000 B2 | 8/2003 | Lu | |
| 6,643,548 B1 * | 11/2003 | Mai et al. | 607/17 |
| 6,768,919 B2 * | 7/2004 | Starobin et al. | 600/520 |
| 6,865,420 B1 | 3/2005 | Kroll | |
| 2003/0045908 A1 | 3/2003 | Condie et al. | |
| 2003/0060854 A1 | 3/2003 | Zhu | |
| 2003/0204209 A1 * | 10/2003 | Burnes et al. | 607/14 |
| 2004/0088017 A1 | 5/2004 | Sharma et al. | |
| 2004/0133247 A1 | 7/2004 | Stahmann et al. | |
| 2005/0137631 A1 | 6/2005 | Yu et al. | |
| 2005/0177194 A1 | 8/2005 | Bjorling | |

FOREIGN PATENT DOCUMENTS

EP   0879618 A1   11/1998
WO   WO09831279 A   7/1998

OTHER PUBLICATIONS

International Search Report, PCT/US2007/065733, Nov. 9, 2007, 7 Pages.

* cited by examiner

*Primary Examiner* — Scott M Getzow
*Assistant Examiner* — Joseph M Dietrich
(74) *Attorney, Agent, or Firm* — Stephen W. Bauer; Reed A. Duthler

(57) ABSTRACT

An implantable medical device (IMD) performs periodic testing of a patient to determine ischemia threshold information. At selected times while the patient is at rest, the IMD increases the pacing rate over time until it receives feedback either from the patient or from an ischemia sensor. The IMD determines the threshold based upon the pacing rate at the time when the feedback was received. The threshold information can be used to adjust the upper pacing rate that can be used during rate adaptive pacing, to determine the effects of drug therapy, and to provide a general indication of the state of coronary artery disease in the patient. The periodic increase of pacing rate to the ischemic zone also provides a preconditioning of the myocardium to allow the patient greater exercise benefit without angina.

21 Claims, 2 Drawing Sheets

IMPLANTABLE MEDICAL DEVICE WITH AUTOMATIC ISCHEMIA THRESHOLD DETERMINATION

BACKGROUND OF THE INVENTION

The present invention relates to implantable medical devices (IMDs), and in particular to devices for automatically determining and monitoring an ischemia threshold in patients suffering from coronary artery disease.

Ischemia occurs when the myocardial demand for oxygen exceeds the delivery capacity of the cardiac circulation. Coronary artery disease (CAD) is the largest cardiovascular comorbidity in patients with implanted pacemakers and defibrillators. The most common symptom of patients with CAD is stable angina, an episode of myocardial ischemia accompanied with symptoms. One hallmark of stable angina is the reproducibility of the symptoms at specific workloads.

Many implantable pacemakers and cardioverter/defibrillators feature rate-responsive pacing, in which the pacing rate is adjusted upward as a function of sensed activity (either alone or in conjunction with sensed respiration). For patients having CAD, rate-adaptive pacing can result in a pacing rate that exceeds the ability of the patient's heart to supply sufficient blood flow to the myocardium. As a result, a CAD patient can be paced beyond a patient's ischemic threshold.

Devices have been proposed that sense ischemia, and reduce the pacing rate when ischemia is detected. Examples of devices including ischemia detectors include Ekwall U.S. Pat. No. 6,256,538, Ekwall, et al. U.S. Pat. No. 6,264,606, Lu U.S. Pat. No. 6,604,000, Kroll U.S. Pat. No. 6,865,420, Zhu Publication No. US 2003/0060854, Stahmann, et al. Publication No. US 2004/0133247 and Yu, et al. Publication No. US 2005/0137631.

BRIEF SUMMARY OF THE INVENTION

A cardiac rhythm management device periodically determines the ischemic threshold of the patient having coronary artery disease while the patient is at rest. The device increases the pacing rate over time until a feedback signal is received, either from the patient, or from an ischemia sensor.

The ischemia threshold information, which is determined based on the pacing rate at the time when the feedback signal was received, can be used for monitoring, diagnostic, and therapeutic purposes. By storing the threshold information gathered from tests over time, information relating to the state of the patient's coronary artery disease can be obtained. Changes in the measured ischemic threshold can be used to evaluate the effects of various types of therapy, including drug therapy. The threshold information can also be used to adjust the upper pacing rate limit, so that rate adaptive pacing does not enter the ischemic zone. In addition, the periodic increase in pacing rate while the patient is at rest provides cardiovascular exercise, and preconditions the myocardium.

DETAILED DESCRIPTION

Figure 1:
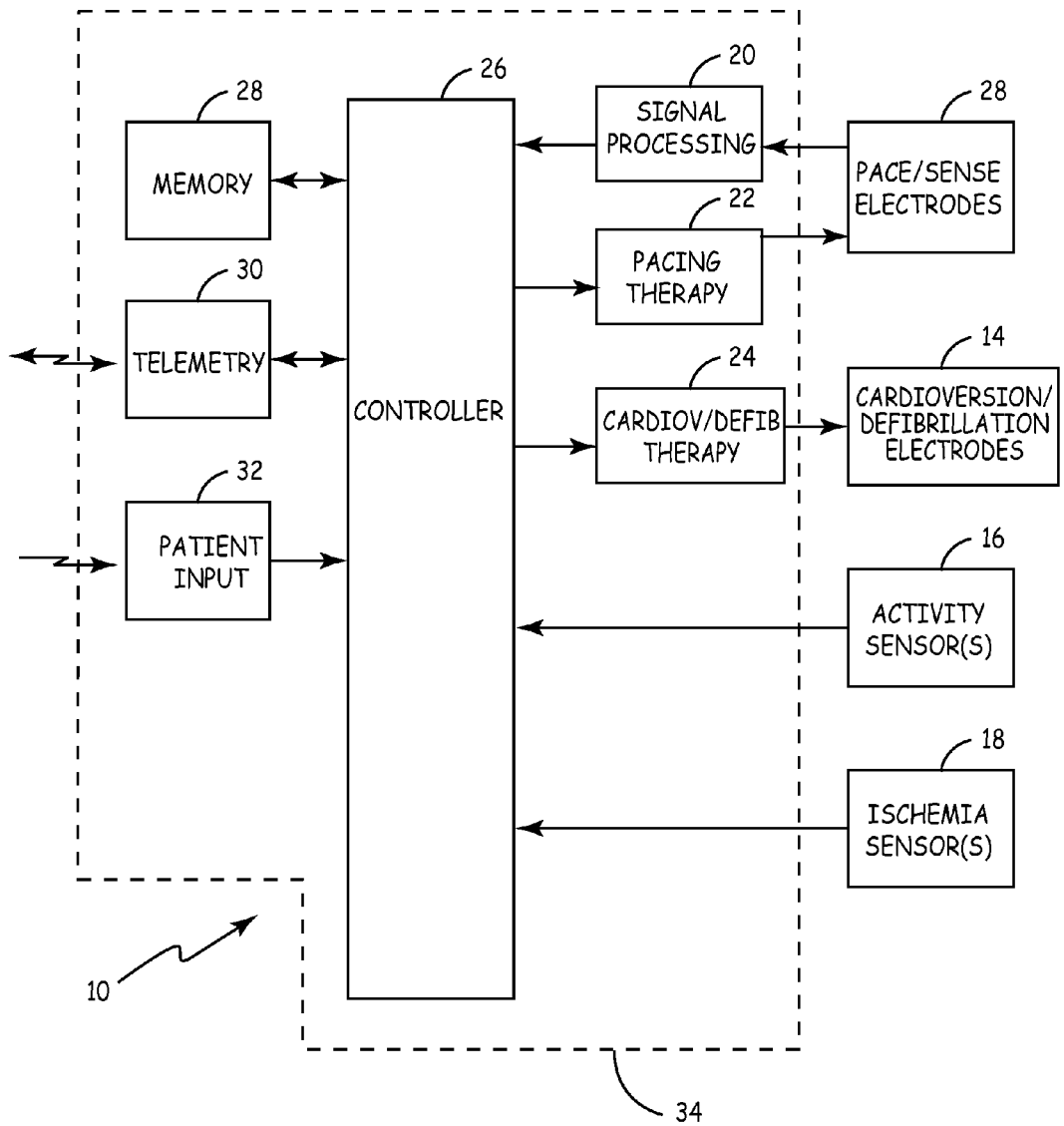
FIG. 1 is a block diagram showing an implantable medical device for performing automatic ischemic threshold testing.

FIG. 1 shows implantable cardiac rhythm management device 10, which includes pace/sense electrodes 12, cardioversion/defibrillation electrodes 14, activity sensor 16, ischemia sensor 18, signal processing circuitry 20, pacing therapy circuitry 22, cardioversion/defibrillation therapy delivery circuit 24, controller 26, memory 28, telemetry circuit 30, patient input sensor 32, and housing 34. Device 10, in this embodiment, is configured to provide pacing therapy through electrodes 12 as well as cardioversion or defibrillation shock therapy through electrodes 14, based upon cardiac activity sensed by electrodes 12.

The pacing therapy can be delivered to a single chamber or to multiple chambers of the patient's heart, depending upon the number and location of pace/sense electrodes 12. Electrodes 12 and 14 may be carried, for example, on electrical leads which extend from housing 34 to positions adjacent to or within the heart. Alternatively, an array of electrodes 12 can be located on exterior surfaces of housing 34. A Can electrode, formed by housing 34, can also be used as one of the cardioversion/defibrillation electrodes.

Electrodes 12 sense electrical activity of the heart, and provide the sense signals to signal processing circuit 20. The processed signals can include an electrogram (EGM) signal representing the waveform of the sensed electrical activity, as well as signals identifying sensed events such as a P-wave (representing atrial depolarization) or an R-wave (representing ventricular depolarization).

Controller 26 uses the signals from signal processing circuit 20 to derive heart rate information and to determine the appropriate pacing therapy to be delivered by pacing therapy circuit 22 to electrodes 12. The particular pacing therapy delivered, and the pacing rate to be used, is determined based upon program information stored in memory 28.

Controller 26 receives inputs representing sensed activity, as indicated by activity sensor(s) 16. The activity inputs can include signals from one or more accelerometers indicating physical movement of the patient, and can also include signals from a minute ventilation sensor indicating respiration rate. Controller 26 can provide rate-responsive pacing, so that when the patient is active, the pacing rate increases appropriately.

Controller 26 also determines when a tachycardia condition exists, based upon the input signals from signal processing circuit 20. Upon detecting a tachycardia condition requiring cardioversion or defibrillation, controller 26 controls therapy circuit 24 to provide a shocking pulse to the heart through electrodes 14.

Ischemia sensor(s) 18 can take a number of different forms, including electrical sensors (e.g. ST segment sensors), chemical sensors (e.g. oxygen and pH sensors), biological marker sensors (e.g. troponin-C sensors), mechanical sensors (e.g. pressure sensors, microphones and accelerometers). The ischemia sensor(s) can also be housed inside housing 34. In addition, the ischemia sensor can form a part of controller 26 and use EGM waveform data to determine when ischemia is occurring.

Figure 2:
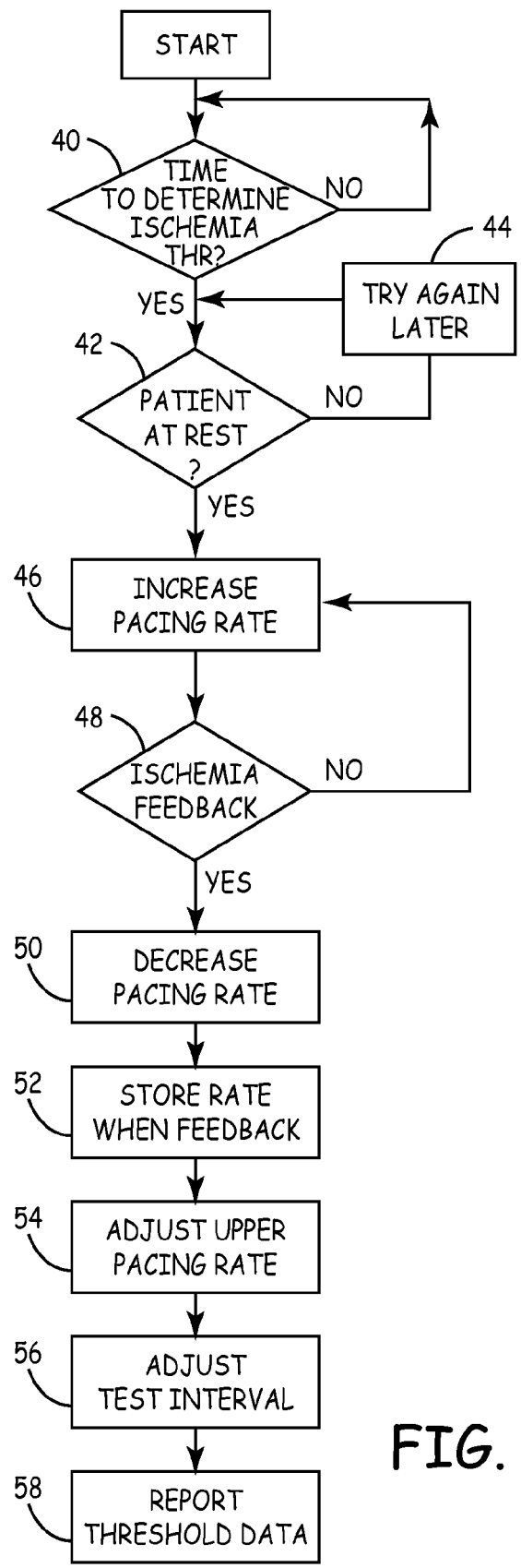
FIG. 2 is a flow chart illustrating a process of performing automatic ischemia threshold testing.

FIG. 2 is a flow diagram illustrating an ischemia threshold determination, which is performed periodically while the patient is at rest. Under Step 40, Controller 26 first determines whether it is time to perform an ischemia threshold test. The tests may be scheduled to occur at a particular time of day, or at particular time intervals.

Under Step 42, if a test is scheduled, controller 26 monitors sensors 16 for indications that the patient is in a low activity or rest condition. The heart rate determined based upon input signals from signal processing circuit 20 can also be used by controller 26 to determine that the patient is at rest. If the patient is not at rest, controller 26 will try again at a later time. (Step 44).

If the patient is at rest, controller 26 initiates the ischemic threshold test. Controller 26 causes therapy circuit 22 to gradually increase the pacing rate of the pacing pulses delivered to electrodes 12. (Step 46). Controller 26 may choose to pace only one chamber, (for example the right atrium) at the increased pacing rate, or may provide multiple chamber pacing, depending upon the particular pacing therapy being used with that patient.

Controller 26 continues to increase the pacing rate until controller 26 either detects ischemia based upon input signals from ischemia sensors 18, or receives feedback in the form of patient feedback from patient input detector 32. (Step 48). The patient can provide feedback, for example, by holding a magnet over the chest near housing 34, so that the patient input detector 32 senses the magnetic field. Alternatively, the patient can provide an RF signal to telemetry circuit 30, indicating to controller 26 that the patient is experiencing pain as a result of the increased pacing rate. In still another alternative, the patient feedback can be in the form of taps on housing 34.

When controller 26 receives an ischemia feedback indication, either based upon detected ischemia or patient feedback, it halts the increase in pacing rate, and then begins a process of decreasing the pacing rate delivered by pacing therapy circuit 22. (Step 50). Controller 26 may decrease the pacing rate on a gradual basis to insure that the myocardium is continuing to receive adequate blood flow while the patient's heart rate is being reduced back to an at rest pacing rate.

Controller 26 stores ischemia threshold information representing the pacing rate at the time when an ischemia feedback indication was received. (Step 52). The threshold information is stored in memory 28.

The threshold information can be used for a number of different monitoring, diagnostic and therapeutic purposes. Controller 26 can adjust the upper pacing rate limit for rate adaptive pacing based upon the most recent ischemia threshold information obtained by testing. (Step 54). As a result, rate adaptive pacing is controlled with foreknowledge of the ischemic threshold, so that pacing can come near but not exceed the ischemic threshold.

Controller 26 can adjust the frequency of testing based upon whether the ischemic threshold is changing or is stable. For example, controller 26 may progressively increase the time interval between tests if a pattern of stable ischemic threshold values result from the testing. (Step 56). This saves on computational activity, as well as energy used in increased pacing therapy during testing. It also minimizes patient discomfort for patients who experience symptomatic ischemia. Once a change in ischemic threshold is detected, more frequent testing can then follow.

By storing ischemic threshold information gathered through periodic testing, changes in the coronary artery disease of the patient can be monitored and evaluated. In addition, the effects of particular types of therapy can be evaluated. For example, drug therapy can be evaluated by evaluating the trends in the stored threshold data collected by periodic automatic testing of the ischemic threshold. For drug therapy evaluation, periodic testing may need to be conducted several times a day. Controller 26 can report the stored threshold data through telemetry circuitry 30 to an external device on a periodic basis, or when interrogated by the external device. (Step 58).

The ischemic threshold information gathered through periodic testing can also be used to adjust the thresholds for the ischemic sensors. For example, if a new ischemic threshold is established based on patient feedback, thresholds in the automatic algorithms in the device may be adjusted to reflect the new ischemic threshold.

The periodic testing of ischemic threshold has another therapeutic effect. By increasing the patient's heart rate while the patient is at rest, the patient receives the benefits of a cardiovascular exercise, without corresponding physical activity. In addition, raising the pacing rate to the ischemic threshold may aid in preconditioning the myocardium and raising the ischemic threshold slightly so the patient can obtain greater exercise benefit without angina.

The patient feedback through patient input detector 32 can also be used during other times, when a threshold test is not being performed. When the patient feedback is received, controller 26 can store the current pacing rate for later use in determining the ischemia threshold. Controller 26 can also reduce the pacing rate in response to the patient feedback, in the same way it reduces pacing rate during an ischemia threshold test.

Although the present invention has been described with reference to preferred embodiments, workers skilled in the art will recognize that changes may be made in form and detail without departing from the spirit and scope of the invention.

The invention claimed is:

1. An implantable medical device (IMD) comprising:
at least a pair of pacing electrodes;
a pacing therapy delivery circuit operatively coupled to the pacing electrodes and configured to provide pacing signals to the pacing electrodes at a pacing rate;
a patient activity sensor coupled to the pacing therapy delivery circuit;
a patient input detector adapted to receive a patient-triggered telemetry signal;
an ischemia sensor; and
controller means for controlling operation of the pacing therapy delivery circuit, wherein the controller means periodically causes an ischemia threshold test to be performed when the patient activity sensor indicates a patient is at rest, wherein the controller means causes the pacing therapy delivery circuitry to increase the pacing rate over time until a feedback signal from either the patient input detector or the ischemia sensor is received, then causes the pacing therapy delivery circuitry to decrease the pacing rate, and causes an ischemia threshold value to be stored based upon the pacing rate at the time the feedback signal was received, wherein the controller adjusts an upper pacing rate limit for the pacing therapy delivery circuit based upon the ischemia threshold value.

2. An IMD according to claim 1 wherein the patient activity sensor provides a signal that is a function of at least one of patient posture, patient movement, patient respiration rate, and patient heart rate.

3. An IMD according to claim 1, wherein the ischemia sensor comprises at least one of an electrical sensor, a chemical sensor, a biological marker sensor, and a mechanical sensor.

4. An IMD according to claim 1, wherein the patient input detector is responsive to an externally generated signal.

5. An IMD according to claim 1, wherein the controller determines timing of a next ischemia threshold test based upon a comparison of the ischemia threshold values from different tests.

6. An IMD according to claim 1, wherein the controller causes ischemia threshold values to be transmitted by telemetry.

7. A method of performing ischemia threshold testing of a patient with coronary artery disease, the method comprising:
   determining that the patient is at rest;
   increasing a pacing rate of pacing signals delivered to the patient in response to a determination that the patient is at rest;
   receiving a feedback signal;
   decreasing the pacing rate of the pacing signals; and
   storing an ischemia threshold value based upon the pacing rate when the feedback signal was received; and
   adjusting an upper pacing rate limit for rate-adaptive pacing based upon the ischemia threshold value.

8. A method according to claim 7, further comprising:
   adjusting a time interval until a next test based on the ischemia threshold value.

9. A method according to claim 8, wherein the time interval until a next test is based upon a comparison of the ischemia threshold value with at least one value derived from a preceding test.

10. A method according to claim 7, wherein the feedback signal is produced by an ischemia detector.

11. A method according to claim 7, wherein the feedback signal is a patient generated signal.

12. A method according to claim 7, further comprising:
   reporting ischemia threshold values representing results of a series of tests.

13. A method of determining an ischemia threshold of a patient, the method comprising:
   determining whether the patient is at rest;
   providing pacing pulses at an increasing pacing rate in response to the determination that the patient is at rest until ischemia is detected; and
   determining an ischemia threshold value based upon the pacing rate when ischemia is detected; and
   determining an upper pacing rate limit based upon the ischemia threshold value.

14. A method according to claim 13, further comprising:
   decreasing the pacing rate after ischemia is detected.

15. A method according to claim 13, further comprising:
   selecting a time interval until a next test based upon the ischemia threshold value.

16. A method according to claim 13, further comprising:
   reporting data representing ischemia threshold values determined during a series of tests.

17. An implantable medical device (IMD) comprising:
   at least a pair of pacing electrodes;
   a pacing therapy delivery circuit operatively coupled to the pacing electrodes and configured to provide pacing signals to the pacing electrodes at a pacing rate;
   an ischemia sensor providing a feedback signal;
   a patient activity sensor coupled to the pacing therapy delivery circuit; and
   controller means for controlling operation of the pacing therapy delivery circuit, wherein, responsive to the patient activity sensor indicating the patient is at rest the controller means causes the pacing therapy delivery circuitry to increase the pacing rate over time until a feedback signal from the ischemia sensor is received, then causes the pacing therapy delivery circuitry to decrease the pacing rate, and causes an ischemia threshold value to be stored based upon the pacing rate at the time the feedback signal was received; and
   wherein the controller adjusts an upper pacing rate limit for the pacing therapy delivery circuit based upon the ischemia threshold value.

18. An IMD according to claim 17, wherein the patient activity sensor provides a signal that is a function of at least one of patient posture, patient movement, patient respiration rate, and patient heart rate.

19. An IMD according to claim 17, wherein the ischemia sensor comprises at least one of an electrical sensor, a chemical sensor, a biological marker sensor, and a mechanical sensor.

20. An implantable medical device (IMD) comprising:
   at least a pair of pacing electrodes;
   a pacing therapy delivery circuit operatively coupled to the pacing electrodes and configured to provide pacing signals to the pacing electrodes at a pacing rate;
   a patient activity sensor coupled to the pacing therapy delivery circuit;
   a patient input detector adapted to receive a patient-triggered feedback signal;
   controller means for controlling operation of the pacing therapy delivery circuit, wherein, responsive to the patient activity sensor indicating the patient is at rest the controller means causes the pacing therapy delivery circuitry to increase the pacing rate over time until a feedback signal from the patient input detector is received, then causes the pacing therapy delivery circuitry to decrease the pacing rate, and causes an ischemia threshold value to be stored based upon the pacing rate at the time the feedback signal was received; and
   wherein the controller adjusts an upper pacing rate limit for the pacing therapy delivery circuit based upon the ischemia threshold value.

21. An IMD according to claim 20, wherein the patient activity sensor provides a signal that is a function of at least one of patient posture, patient movement, patient respiration rate, and patient heart rate.

* * * * *